United States Patent
Delin

(10) Patent No.: US 8,956,316 B2
(45) Date of Patent: Feb. 17, 2015

(54) KNEE ORTHOSIS FOR TORN ANTERIOR CRUCIATE LIGAMENT

(76) Inventor: Cyrille Delin, Boulogne Billancourt (FR)

( * ) Notice: Subject to any disclaimer, the term of this patent is extended or adjusted under 35 U.S.C. 154(b) by 228 days.

(21) Appl. No.: 13/574,313

(22) PCT Filed: Jan. 25, 2011

(86) PCT No.: PCT/FR2011/050138
§ 371 (c)(1), (2), (4) Date: Jul. 20, 2012

(87) PCT Pub. No.: WO2011/092423
PCT Pub. Date: Aug. 4, 2011

(65) Prior Publication Data
US 2012/0296251 A1    Nov. 22, 2012

(30) Foreign Application Priority Data
Jan. 26, 2010   (FR) ...................................... 10 50518

(51) Int. Cl.
*A61F 5/00*     (2006.01)
*A61F 5/01*     (2006.01)

(52) U.S. Cl.
CPC ....... *A61F 5/0125* (2013.01); *A61F 2005/0167* (2013.01); *A61F 2005/0179* (2013.01)
USPC .................. 602/26; 602/20; 602/23

(58) Field of Classification Search
USPC .............................. 602/16, 23, 26, 60–62, 20; D24/190–192
See application file for complete search history.

(56) References Cited

U.S. PATENT DOCUMENTS 2,270,685 A   1/1942  Miller
5,417,647 A   5/1995  Down

FOREIGN PATENT DOCUMENTS

DE        34 22 685 A1    12/1958
DE        198 44 545 A1    3/2000
WO        2009/149217 A2  12/2009

OTHER PUBLICATIONS

International Search Report for PCT/FR2011/050138 dated Jun. 1, 2011.

*Primary Examiner* — Alireza Nia
*Assistant Examiner* — Keri J Nelson
(74) *Attorney, Agent, or Firm* — Heslin Rothenberg Farley & Mesiti P.C.

(57) ABSTRACT

The orthosis includes an articulated framework made to be fixed on either side of the knee onto the thigh and lower leg, restraint straps attached to the framework and surrounding the thigh and lower leg leaving the patellar area free. The straps cross and are superimposed on each other on the posterior side next to the skin of the popliteal fossa at the same level as the center of rotation of the knee in order to prevent the anterior part of the tibia sliding forward. Each strap is held in a rigid guide on the lower leg and the thigh, while, where they cross at the popliteal fossa, they are held together by a non stretching sleeve. The first shortest strap is on the outside, as far posteriorly as possible and the last longest strap is on the inside, as far anteriorly as possible next to the skin of the popliteal fossa.

10 Claims, 4 Drawing Sheets

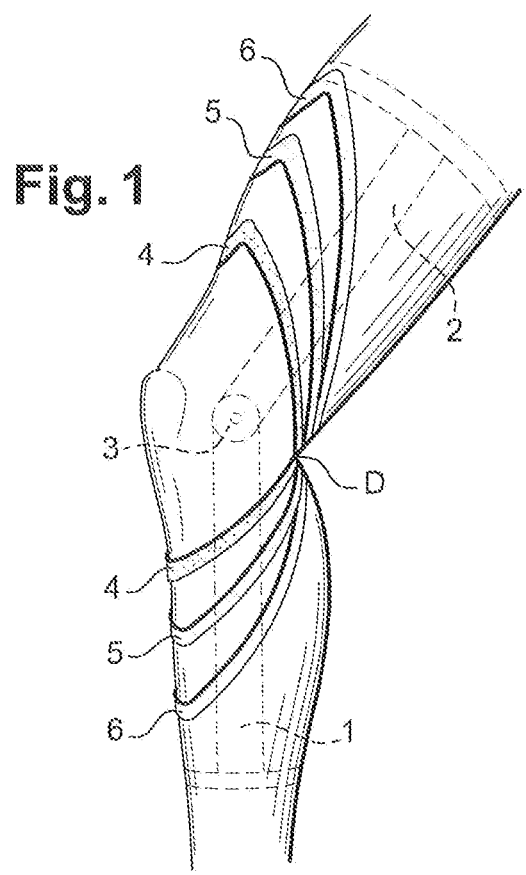
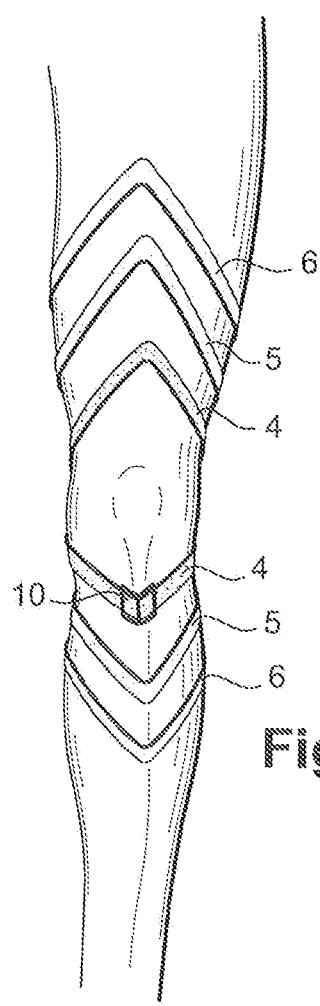
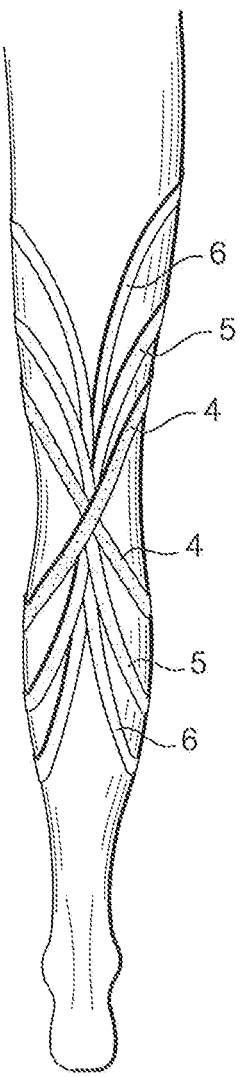
Fig. 1
Fig. 2
Fig. 3

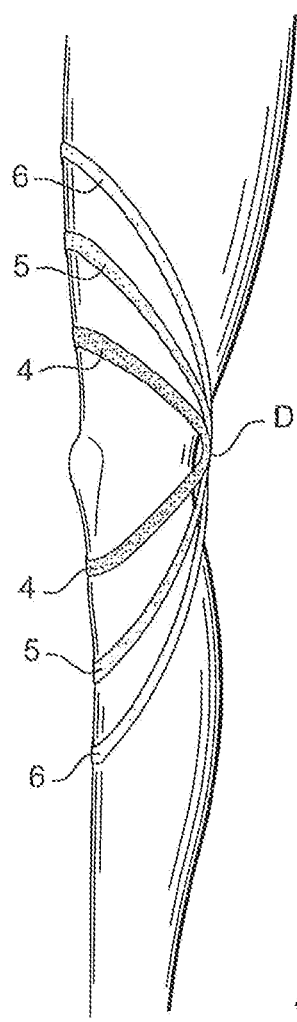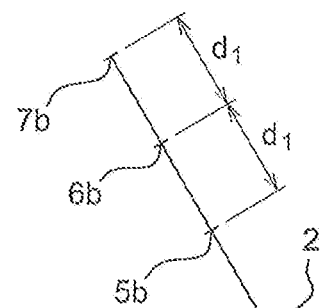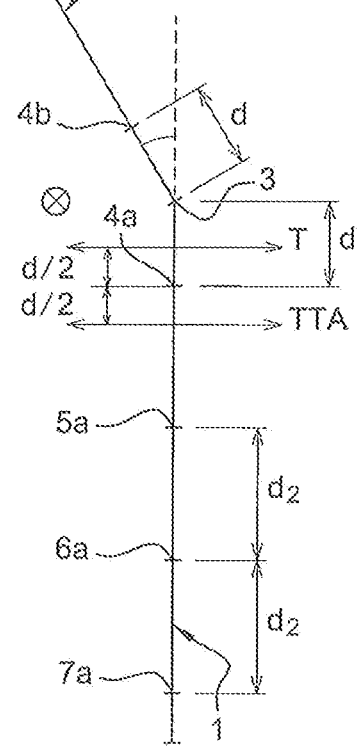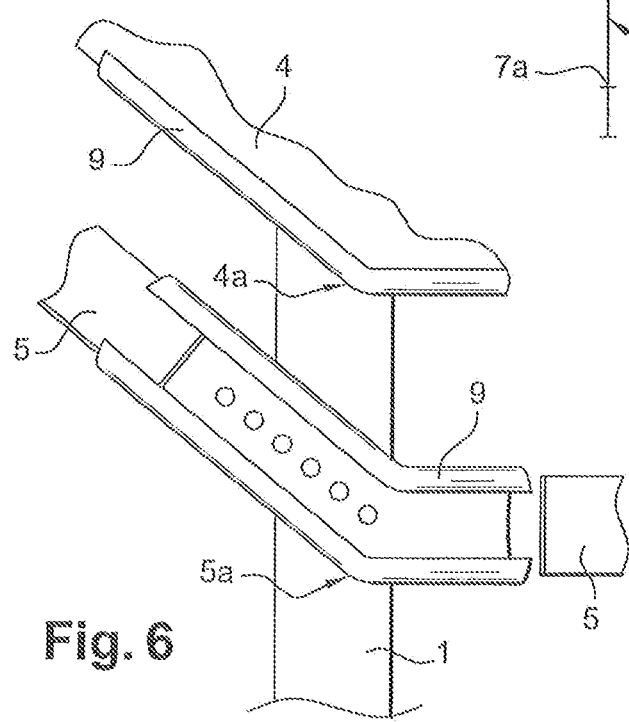

KNEE ORTHOSIS FOR TORN ANTERIOR CRUCIATE LIGAMENT

CROSS REFERENCE TO RELATED APPLICATIONS

This application is a national stage filing under section 371 of International Application No. PCT/FR2011/050138 filed on Jan. 25, 2011, and published in French on Aug. 4, 2011 as WO 2011/092423 A1 and claims priority of French application No. 1050518 filed on Jan. 26, 2010, the entire disclosure of these applications being hereby incorporated herein by reference.

TECHNICAL FIELD OF THE INVENTION

The invention concerns the technical field of orthoses, particularly for the knee.

The invention is particularly advantageously of use for traumatic lesions of the anterior cruciate ligament.

DESCRIPTION OF THE PRIOR ART

It is perfectly well known to anyone working in the field that the anterior cruciate ligament of the knee, extends between the anterior part of the tibial plateau and the internal surface of the external femoral condyle. The basic function of this ligament is to prevent the tibia sliding anteriorly under the femur and to control the rotatory stability of the tibia under the femur, during flexion of the knee.

An anterior cruciate ligament tear leads to instability of the knee and, consequently, risks of dislocation. Therapy for a torn anterior cruciate ligament may involve surgical or functional treatment.

Surgical treatment consists of reconstruction of the anterior cruciate ligament e.g. using a graft taken from a tendon.

Functional treatment consists of compensating the absence of the anterior cruciate ligament by muscular and proprioceptive re-education to maintain the stability of the knee. To ensure this knee stability, it is very often necessary to wear an orthosis, in particular during pivoting activities which make particular demands on the anterior cruciate ligament. This may also be the case after surgical treatment.

Various types of knee orthoses are currently available.

Generally, an orthosis consists of an articulated framework arranged for attachment to the thigh and lower leg, on either side of the knee, with means of stabilising the knee joint against varus and valgus forces. For example, frameworks around the thigh and lower leg are connected by a system of articulated stays with supporting parts approximately at the centre of rotation of the knee.

Nevertheless it has been seen that these various types of orthoses do not reduce the anterior drawer effect which is present in a complete anterior cruciate ligament tear.

The objective of the invention is to remedy these disadvantages in a simple, safe, effective and rational manner.

DESCRIPTION OF THE INVENTION

The invention proposes to solve the problem by preventing the anterior and superior part of the tibia sliding forward, by using an orthosis.

To solve such a problem, an orthosis has been designed and perfected which includes an articulated framework to be fixed to the thigh and lower leg, on either side of the knee. According to the invention, this orthosis includes means of restraint in the form of straps, attached to the said framework, and able to surround the thigh and the lower leg leaving the patellar area free and crossing and superimposing on each other on the posterior side against the skin of the popliteal fossa at the level of the centre of rotation of the knee, in order to avoid the anterior part of the tibia sliding forward. Each strap is helf in a rigid guide on the lower leg and thigh while where they cross in the popliteal fossa, the straps are held together by a non stretching sleeve, the first strap, the shortest, being on the outside, as far posteriorly as possible and the last strap, the longest, being on the inside, as far forward as possible next to the skin of the popliteal fossa.

The means of restraint consist of several straps attached as previously indicated, i.e. one, two, three, four or more in number, depending on the pathological condition to be treated and the morphology of the patient.

Advantageous results have been obtained with four straps suitably positioned on the lower leg and thigh, under the following conditions:

- A first strap is positioned on the lower leg and relative to the centre of rotation of the knee, at an equal distance from the tibial plateau and the anterior tibial tuberosity and, on the thigh, approximately at a defined distance from the centre of rotation of the knee. The posterior part of the lower rigid guide holding this first strap in place is positioned on the lower leg approximately at an angle of about 65° relative to the tibial axis, while on the thigh, the posterior part of the upper rigid strap guide is positioned at an angle of approximately 72° relative to the femoral axis.
- A second strap is positioned on the thigh at approximately 4 times the distance of the first strap to the centre of rotation of the knee and on the lower leg, at approximately 1.5 times this distance. The posterior part of the lower rigid guide holding this second strap is positioned on the lower leg at an angle of approximately 48° relative to the tibial axis, and on the thigh, the posterior part of the upper rigid strap guide is positioned at an angle of approximately 40° relative to the femoral axis.
- A third strap is positioned on the thigh and lower leg at equal distances between the second strap and a fourth strap. The posterior part of the lower rigid guide of this third strap is positioned on the lower leg at an angle of approximately 39° relative to the tibial axis, while on the thigh, the posterior part of the upper rigid strap guide is positioned at an angle of approximately 40° relative to the femoral axis. The posterior part of the lower rigid guide of the fourth strap is positioned on the lower leg at an angle of approximately 35° relative to the tibial axis, while on the thigh, the posterior part of the upper rigid strap guide is positioned at an angle of approximately 40° relative to the femoral axis.

Other characteristics of the orthosis:

- On the lower leg, the posterior ends of the lower rigid guides of the second, third and fourth straps are on a line at an angle of approximately 20° to the tibial axis, whereas the posterior end of the lower rigid guide of the first strap is on a line forming an angle of approximately 15° relative to the tibial axis.
- On the thigh, the posterior ends of the second, third and fourth straps are on a line at an angle of approximately 20° to the femoral axis, whereas the posterior end of the first strap is on a line forming an angle of approximately 15° relative to the femoral axis.

To advantage, in the orthosis according to the invention, from the popliteal fossa the upper and lower strands of the first strap, between the lower leg and thigh, are oriented at an acute angle, the summit of which is where they cross at the back of the knee, whereas the strands of the other straps form an obtuse angle, the summit of which being where they cross at the back of the knee.

To advantage, in the orthosis according to the invention, the first strap, on the anterior side of the tibia, has a rigid part which is suitably shaped to pass over the patellar tendon, resting on the tibia on either side of the latter.

According to different embodiments of the orthosis according to the invention, all of the straps or some of them are elastic or all of the straps are non-elastic.

To advantage and according to another characteristic, just a part of the straps may be elastic. In this case, the first strap is not elastic from the popliteal fossa, but the other straps are elastic with a progressive degree of lengthening.

While still remaining within the framework of the invention, it is possible for all the straps to be elastic or all, non-elastic.

BRIEF DESCRIPTION OF FIGURES

The invention is explained below in more detail using the accompanying figures of drawings in which:

FIG. 1 is a diagrammatic view in profile showing the principle of the orthosis according to the invention in flexion;

FIG. 2 is a view from the front corresponding to FIG. 1;

FIG. 3 is a view from the rear corresponding to FIG. 1;

FIG. 4 is a similar view to FIG. 1 but in extension;

FIG. 5 is a diagrammatic view showing particularly the position of the straps around the lower leg and thigh;

FIG. 6 is a partial view showing an example of attachment and adjustment of the ends of one of the straps to a support provided by part of the framework;

DETAILED DESCRIPTION OF A PREFERRED EMBODIMENT OF THE INVENTION

Figure 11:
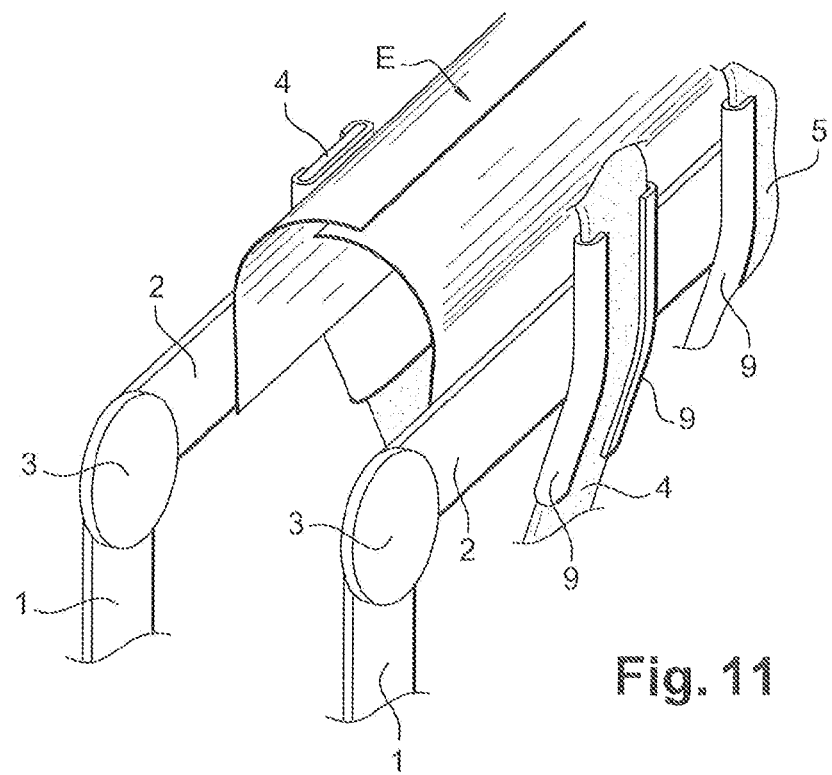
FIG. 11 is a diagrammatic partial view in perspective at thigh level of a non-limiting example illustrating an orthosis with restraining straps according to the characteristics of the invention.

FIG. 11 is a non-limiting illustration of a framework for a knee orthosis. For example, this framework has two symmetrical arms (1) and (2) articulating at (3), approximately at the level of the centre of rotation of the knee. The two arms (1) and (2) are arranged, indeed in a well-known manner, on either side of the lower leg and thigh, being held in place by any known and appropriate means, such as fabric envelopes (E) with the means for temporarily joining them, e.g. hook and loop tape.

According to a basic characteristic of the invention, this framework, irrespective of how it is produced, has means of restraint in the form of straps (4), (5), (6) and (7) previously positioned and oriented, as set out in the description below, so as to surround the lower leg and thigh, leaving the patellar area free and which cross and are superimposed on each other on the posterior side against the skin of the popliteal fossa, at the level of the centre of rotation of the knee. These straps serve to prevent the anterior and superior part of the tibia sliding forwards. The straps (4), (5), (6) and (7) are held in rigid guides (9) which are part of the framework for the lower leg and thigh.

See particularly FIGS. 1, 2, 3 and 4 which show the position of three straps (4), (5) and (6) relative to the arms (1) and (2) of the framework.

Figure 7:
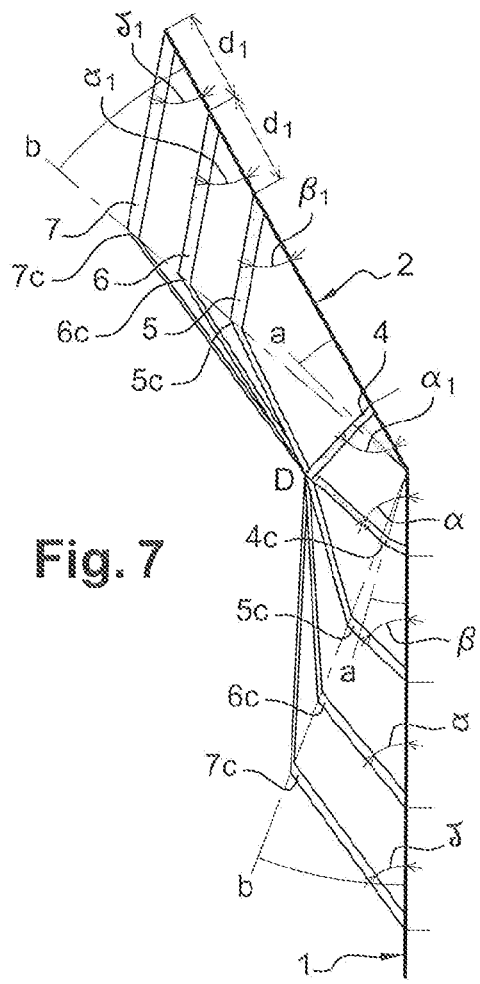
FIG. 7 shows the angles of the straps relative to the lower leg and thigh.

Considering the problem posed of reducing the anterior drawer effect, in other words, of avoiding the anterior and superior part of the tibia sliding forwards as indicated, the straps are positioned, oriented and cross at the level of the popliteal fossa to advantage in the conditions set out hereafter, with reference particularly to the diagrams in FIGS. 5 and 7. These very diagrammatic figures show in particular the arms (1), on the lower leg, and the arms (2) on the thigh and their articulation (3) corresponding approximately to the centre of rotation of the knee. The rigid guides (9) for holding and setting the angles of the different straps are not shown.

The first strap (4) is positioned at (4a) on each arm (1) and, relative to the centre of rotation (3), at an equal distance (d/2) from the tibial plateau (T) and the anterior tibial tuberosity (ATT), and at (4b) on each arm (2), approximately at a distance (d) from the centre of rotation (3). The posterior part of the rigid guide of this first strap (4) is positioned on each arm (1) with an angle ($\alpha$) of about 65° relative to the tibial axis (arm (1)) while on each arm (2), the posterior part of the rigid guide is positioned at an angle ($\alpha 1$) of about 72° relative to the femoral axis (arm (2)) (FIG. 7).

The second strap (5) is positioned at (5b) on each arm (2) at about 4 times the distance (d) and positioned at (5a) on each arm (1) at about 1.5 times the distance (d). The posterior part of the rigid guide of this second strap (5) is positioned on each arm (1), i.e. on the lower leg, at an angle ($\beta$) of about 48° relative to the tibial axis and, on each arm (2) i.e. on the thigh, at an angle ($\beta 1$) of approximately 40° relative to the femoral axis.

In the example illustrated in FIGS. 5 and 7, a third strap (6) is positioned at (6b) on the arms (2), i.e. on the thigh and at (6a) on the arms (1), i.e. on the lower leg, at an equal distance ((d1) for the thigh and (d2) for the lower leg) between the attachment points (5b) and (5a) and those of a fourth strap (7) fixed at (7b) on each arm (2) and at (7a) on each arm (1).

The posterior parts the rigid guides of the third and fourth straps (6) and (7) are positioned on each arm (1) at an angle ($\gamma$) and (6) of 39° and 35° to the tibial axis, respectively, and, on each arm (2), at an angle ($\gamma 1$) and (M) of 40° to the femoral axis.

As FIG. 7 shows, the posterior end (4c) of the rigid guide of the first strap (4), both on the lower leg and the thigh, is on a line (a) at an angle of approximately 15° to the tibial axis (arm (1)) or to the femoral axis. The posterior ends (5c), (6c) and (7c) of the rigid guides of the other straps (5), (6) and (7) are, both on the lower leg and the thigh, on a line (b) making an angle of approximately 20° to the tibial and femoral axes.

Figure 8:
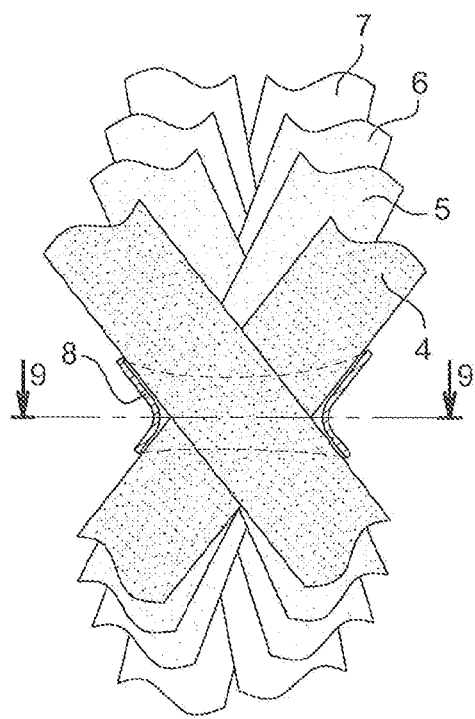
FIG. 8 shows a posterior view of the principle of crossing the straps at the popliteal fossa.
Figure 9:
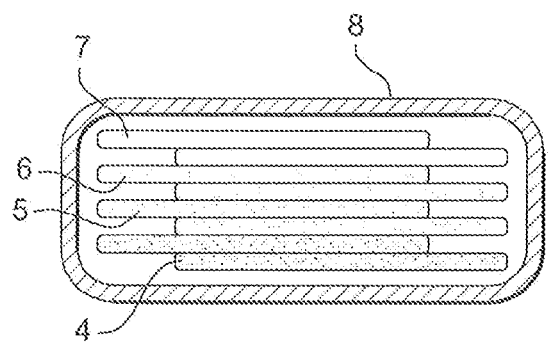
FIG. 9 is a transverse sectional view along the line 9-9 on FIG. 8.

At the popliteal fossa (D), the strands of the first strap (4), between the lower leg and the thigh, make an acute angle, whereas the strands of the other straps (5), (6) and (7) make an obtuse angle. In other words, straps (5), (6) and (7) have an angle contrary to that of strap (4), in order to exert traction on the latter during extension of the knee, preventing the tibial plateau moving forward when the anterior cruciate ligament is torn.

Where they cross posteriorly in the popliteal fossa (D), straps (4), (5), (6) and (7) are held together by a non stretching sleeve (8). The first strap (4) is on the outside, i.e. as far posteriorly as possible (FIGS. 8 and 9). The last strap (7) (the longest) is on the inside, as far anteriorly as possible, next to the skin of the popliteal fossa.

To advantage, according to another characteristic, the first strap (4) is not elastic in the sense that it does not or barely stretches, whereas the other straps (5), (6) and (7) are elastic with a progressive degree of lengthening.

Obviously, attachment and positioning at the various areas (4a)-(4b), (5a)-(5b), (6a)-(6b) and (7a)-(7b), on each of the arms (1) and (2) of the framework, is by any known means under the conditions given previously. For example, the straps (4), (5), (6) and (7) are attached separately, so that they can be adjusted by sliding them and locking them in position, in the rigid guides (9) arranged at the various places on arms (1) and (2) mentioned previously.

Figure 10:
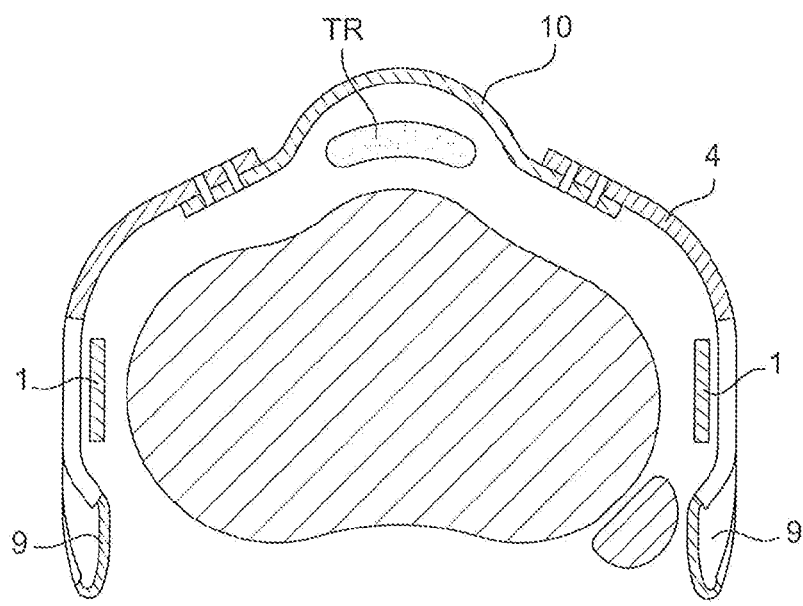
FIG. 10 is a partial section through the inferior anterior part of the first strap, on a larger scale.

It should also be noted that, as shown in FIG. 10, a part of the strap (4), on the anterior side over the tibia, is fastened to a rigid part (10) shaped approximately like an arch or omega in order to pass over the patellar tendon (PT), finding support on either side of the latter.

The advantages are clear from the description: in particular it is emphasized that due to the position and crossing point of the straps, the strap restraint system prevents the anterior and superior part of the tibia from sliding forward (anterior drawer effect) when the anterior cruciate ligament is completely torn.

In short, as already stated, the number of straps may be varied depending on the height and musculature of the patient, and the effect desired. The same applies to the different degrees of elongation of the straps, which may be non-elastic.

Finally, the strap system may be attached to any type of framework known which has an anterior part that is rigid.

The invention claimed is:

1. A knee orthosis for anterior cruciate ligament tears comprising an articulated framework adapted to be fixed to a thigh and lower leg, on either side of the knee, when worn, restraint straps attached to said framework, each restraint strap adapted to surround both the thigh and lower leg leaving a patellar area free and crossing and superimposing on each other on a posterior side in a vicinity of the popliteal fossa at a level of center of rotation of the knee in order to avoid an anterior part of a tibia sliding forward, each strap being held on the lower leg and thigh by a respective rigid guide of the framework, while where the straps cross in the vicinity of the popliteal fossa, the straps are held together by a non stretching sleeve, a first shortest strap of said restraint straps being on an outside, as posteriorly as possible and a last longest strap of said restraint straps being on an inside, as far forward as possible and closest to skin of the popliteal fossa, wherein the first strap is adapted to be positioned on the lower leg and relative to the center of rotation of the knee, at an equal distance (d/2) from a tibial plateau and an anterior tibial tuberosity and, on the thigh, approximately at a first distance (d) relative to the center of rotation of the knee, a posterior part of the rigid guide holding the first strap being positioned on the lower leg at an angle of approximately 65° to a tibial axis and, on the thigh, at an angle of approximately 72° to a femoral axis, and wherein a second strap of the restraint straps is adapted to be positioned on the thigh at approximately 4 times the first distance (d) of the first strap from the center of rotation of the knee and, on the lower leg, at approximately 1.5 times the first distance (d), a posterior part of the rigid guide of the second strap being positioned on the lower leg at an angle of approximately 48° to the tibial axis and on the thigh at an angle of approximately 40° to the femoral axis.

2. The knee orthosis according to claim 1, wherein a third strap of the restraint straps is adapted to be positioned on the thigh and lower leg at equal distances between the second strap and the last strap, a posterior part of the rigid guide of the third strap being oriented on the lower leg at an angle of approximately 39° to the tibial axis and on the thigh at an angle of approximately 40° to the femoral axis.

3. The knee orthosis according to claim 2, wherein a posterior part of the rigid guide of the last strap is oriented on the lower leg at an angle of approximately 35° to the tibial axis and on the thigh at an angle of approximately 40° to the femoral axis.

4. The knee orthosis according to claim 3, wherein, on the thigh and lower leg, the posterior ends of the rigid guides of the second, third and last straps are on a line at an angle of approximately 20° to the femoral or tibial axis, while the posterior end of the first strap is on a line forming an angle of approximately 15° with the femoral or tibial axis.

5. The knee orthosis according to claim 1, wherein upper and lower strands of the first strap, between the lower leg and thigh, make an acute angle where said strands cross in the vicinity of the popliteal fossa, the summit of which is where they cross at the back of the knee, while strands of the other straps form an obtuse angle, the summit of which being where they cross at the back of the knee.

6. The knee orthosis according to claim 1, wherein all or part of the straps are elastic.

7. The knee orthosis according to claim 6, wherein the first strap is not elastic, the other straps being elastic with a progressive degree of lengthening.

8. The knee orthosis according to claim 1, wherein all the straps are non-elastic.

9. A knee orthosis for anterior cruciate ligament tears comprising an articulated framework adapted to be fixed to a thigh and lower leg, on either side of the knee, when worn, restraint straps attached to said framework, each restraint strap adapted to surround both the thigh and lower leg leaving a patellar area free and crossing and superimposing on each other on a posterior side in a vicinity of the popliteal fossa at a level of center of rotation of the knee in order to avoid an anterior part of a tibia sliding forward, each strap being held on the lower leg and thigh by a respective rigid guide of the framework, while where the straps cross in the vicinity of the popliteal fossa, the straps are held together by a non stretching sleeve, a first shortest strap of said restraint straps being on an outside, as posteriorly as possible and a last longest strap of said restraint straps being on an inside, as far forward as possible and closest to skin of the popliteal fossa, wherein the first strap, on an anterior side on a tibia, has a shaped rigid part passing over a patellar tendon, resting on the tibia on either side of the patellar tendon.

10. A knee orthosis for anterior cruciate ligament tears comprising an articulated framework adapted to be fixed to a thigh and lower leg, on either side of the knee, when worn, restraint straps attached to said framework, each restraint strap adapted to surround both the thigh and lower leg leaving a patellar area free and crossing and superimposing on each other on a posterior side in a vicinity of the popliteal fossa at a level of center of rotation of the knee in order to avoid an anterior part of a tibia sliding forward, each strap being held on the lower leg and thigh by a respective rigid guide of the framework, while where the straps cross in the vicinity of the popliteal fossa, the straps are held together by a non stretching sleeve, a first shortest strap of said restraint straps being on an outside, as posteriorly as possible and a last longest strap of said restraint straps being on an inside, as far forward as possible and closest to skin of the popliteal fossa, wherein ends of the straps are held separately so that they can be adjusted by sliding and locking the ends in position in respective rigid guides of the framework.

* * * * *